United States Patent [19]
Okada

[11] Patent Number: 5,617,602
[45] Date of Patent: Apr. 8, 1997

[54] MOTOR-DRIVEN TOOTHBRUSH

[76] Inventor: Eiji Okada, 5-15-5, Nakanobu, Shinagawa-ku, Tokyo, Japan

[21] Appl. No.: 495,092

[22] Filed: Jun. 27, 1995

[51] Int. Cl.$^6$ ..................................................... A46B 13/02

[52] U.S. Cl. .......................... 15/22.1; 15/176.6; 403/333; 403/361

[58] Field of Search ........................ 15/22.1, 145, 176.1, 15/176.6; 403/333, 361

[56] References Cited

U.S. PATENT DOCUMENTS

| | | | |
|---|---|---|---|
| 2,809,846 | 10/1957 | Whiteford | 403/333 |
| 4,575,277 | 3/1986 | Dickey et al. | 403/361 |
| 4,811,445 | 3/1989 | Lagieski et al. | 15/176.1 |
| 5,017,068 | 5/1991 | Cooksey | 403/361 |
| 5,066,162 | 11/1991 | Wall et al. | 403/361 |

FOREIGN PATENT DOCUMENTS

| | | | |
|---|---|---|---|
| 40-12541 | 6/1940 | Japan . | |
| 53-21650 | 2/1978 | Japan | 15/22.1 |
| 53-29847 | 3/1978 | Japan | 15/22.1 |
| 61-217109 | 9/1986 | Japan . | |
| 5-4918 | 1/1993 | Japan . | |
| 5-11829 | 2/1993 | Japan . | |

*Primary Examiner*—David Scherbel
*Assistant Examiner*—Terrence R. Till
*Attorney, Agent, or Firm*—Flynn, Thiel, Boutell & Tanis, P.C.

[57] ABSTRACT

It is an object of the present invention to make an engaging section between a holder section and a toothbrush section of a motor-driven toothbrush more simple, manufacture thereof easier and also minimize the production cost as well as to achieve minimization and weight reduction thereof, and also to improve the reliability of insertion. For this purpose, an engaging/receiving hole or bore is formed in the toothbrush section of the motor-driven toothbrush, and a projection of the holder section is inserted into the engaging hole for fixing the toothbrush section to the holder section. Also the engaging projection is formed on said holder section and the toothbrush section is made of resilient material to provide the engaging hole having a round cross-section into which the projection is inserted. Furthermore the engaging hole is provided with a round cross-section into which the projection formed in said holder section is inserted, said engaging hole having a larger diameter section in the entrance side thereof and a smaller diameter section in the bottom side thereof, and at least one resilient engaging section projecting to a center of the engaging hole is continuously provided in at least one of the larger diameter section in the entrance side of the engaging hole and the smaller diameter section in the bottom side of the engaging hole.

5 Claims, 6 Drawing Sheets

MOTOR-DRIVEN TOOTHBRUSH

FIELD OF THE INVENTION

The present invention relates to a motor-driven toothbrush, and more particularly to a motor-driven toothbrush in which the torque generated by a motor is converted by a torque convertor into a rolling movement or a sliding movement or that based on a vibrating system with a weight for eccentricity set on a rotation shaft of said motor, said motor-driven toothbrush used for cleaning a surface of teeth by contacting the toothbrush section to the teeth surface.

BACKGROUND OF THE INVENTION

Toothbrushes are generally divided into common ones for manual use in which their holder sections and toothbrush sections are monolithically formed and motor-driven ones incorporating a motor driven by a current from a battery or a receptacle.

Motor-driven toothbrushes include those in which the torque generated by the motor is converted by a torque converting mechanism into either a rolling, moving or sliding movement. Still other motor-driven toothbrushes include a vibrating system with a weight that is eccentrically set on a rotational shaft of the motor. Motor-driven toothbrushes of both types have proven to be tools for protecting health of teeth and gums since they both clean the surface of the teeth and massage the gums.

Motor-driven toothbrushes are usually constructed to have a holder section and toothbrush section that can be selectively attached to the holder section. This makes it possible for different persons to use individual toothbrush sections with a common holder section and allow individuals to replace toothbrush sections as they wear out.

In some types of conventional motor-driven toothbrushes, a screwing section and a screwed section are formed in the holder section and toothbrush section, respectively, for securing the sections together. In other conventional motor-driven toothbrushes, two components are fixed to each other with a stopper that includes a resilient member, such as a spring.

The conventional type of motor-driven toothbrushes as described above have the common feature that configuration of a mounting section is complicated.

As a result, it is very difficult to manufacture especially a mounting section of a motor-driven toothbrush. This difficulty has been known to increase the overall cost of manufacturing these toothbrushes.

Also, because the configuration of the mounting section of the motor-driven toothbrush is complicated, both the size and weight of the toothbrush often need to be increased. The increase in these physical characteristics make use of the toothbrush inconvenient.

Still other conventional motor-driven toothbrushes include those which make use of an engaging claw that is different from the screw system or the stopper system. Toothbrushes that include these engaging claws are also complicated. Moreover, there are also some concerns for stability of the holder section after it is set on the toothbrush section, which means that the reliability is disadvantageously low.

SUMMARY OF THE INVENTION

The present invention is designed to eliminate the disadvantages associated with conventional toothbrush holder-toothbrush coupling assemblies. The motor-driven toothbrush of this invention includes a holder section and a toothbrush section engaging the holder section. An engaging hole is formed in an engaging receiving section of the toothbrush section. A complementary engaging projection section is formed in an engaging section of the holder section for insertion into the engaging hole to couple the two sections together.

In some preferred versions of the invention, the toothbrush section is made of resilient material to provide and formed to define an engaging hole with a round cross-section into which the engaging projection section is inserted.

In some versions of the invention, the engaging hole is shaped to have a larger diameter section at the entrance side thereof and a smaller diameter section at the distal side thereof. The portion of the toothbrush holder forming the engaging hole may further be shaped to have at least one engaging key that projects into the center of the engaging hole in either the larger diameter section or the smaller diameter section.

The engaging projection section of a holder section of this invention is inserted into an engaging hole of a toothbrush section to secure the toothbrush section to the holder section. This invention thus simplifies the construction of the engaging section of the holder section and of the toothbrush section of a motor-driven toothbrush. Thus, manufacture of the toothbrush becomes easier, which reduces the cost of manufacture. This invention also offers a toothbrush engaging assembly of reduced size and weight.

Still another advantage of this invention is that the engaging key of the toothbrush section securely clamps the toothbrush section to the holder section to reliably hold the two sections together.

BRIEF DESCRIPTION OF THE DRAWINGS

A detailed description is made hereinafter for embodiments of the present invention with reference to the related drawings.

DETAILED DESCRIPTION

Figure 1:
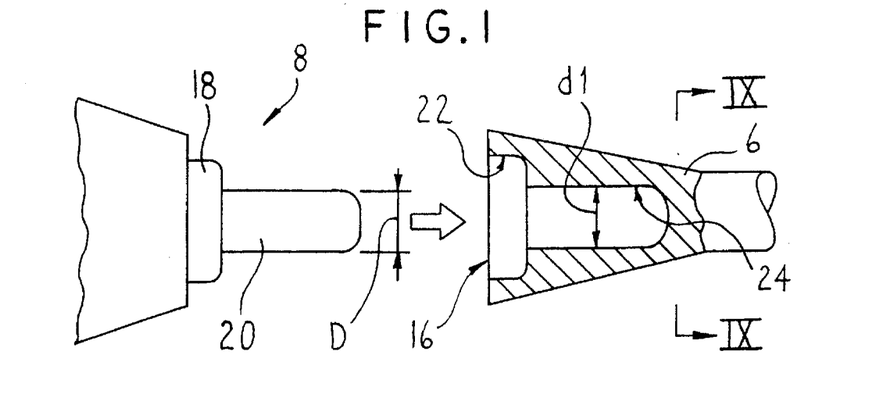
FIG. 1 is an enlarged cross-sectional view illustrating a state where a toothbrush section has been inserted into a holder section of the motor-driven toothbrush according to the first embodiment of the present invention.
Figure 2:
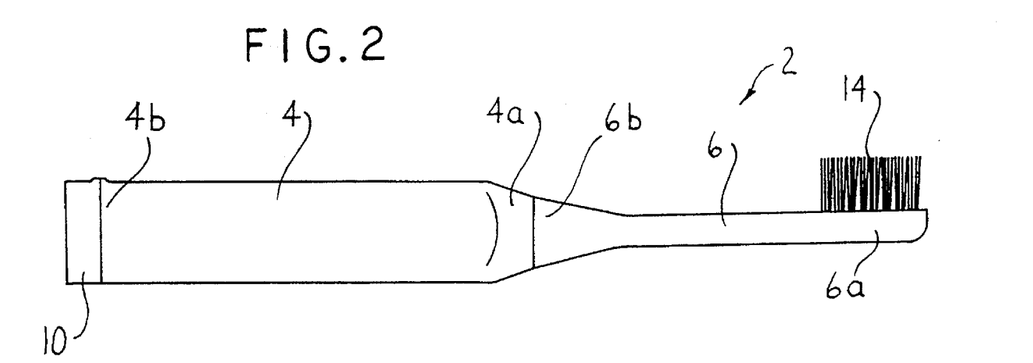
FIG. 2 is a front view of the motor-driven toothbrush.

FIGS. 1 to 9 show a first embodiment of the present invention. In FIG. 2, designated at reference numeral 2 is a motor-driven toothbrush, at 4 a holder section, and at 6 a toothbrush section.

Figure 6:
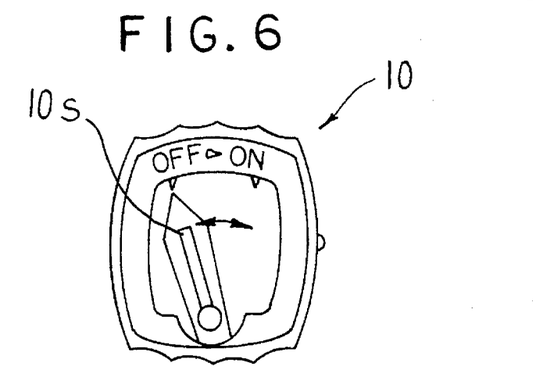
FIG. 6 is a general front view illustrating the cap switch of the motor-driven toothbrush.

The holder section 4 is made of plastic material and has a rectangular shape or a cylindrical shape. An engaging projection section 8 is formed in the side of one end 4a of this holder section 4. A cap 10 having a switch attached thereto is located at the other end 4b of the holder section. The switch on the cap 10 is, as shown in FIG. 6, is an ON position when a lever 10s of the cap 10 is turned clockwise (or moved to the right), and on the contrary the switch is turned OFF if the lever 10s is turned counterclockwise (or fallen to the left).

Also incorporated inside the holder section 4 are a motor (not illustrated), a torque converting mechanism, or a weight for eccentricity is used to transfer the rotational motion of the motor to a vibratory motion in the engaging section 8 (transfer sub-assembly not shown). An AA battery 12 is used to supply the power needed to energize the motor.

The toothbrush section 6 has a base made of plastic material. A brush 14 made with pighair or plastic filament members is provided on one end 6a of the toothbrush section 6. An engaging hole or bore 16 is formed in the other end 6b of the toothbrush section 6.

The engaging projection section 8 of the engaging section of the holder section 4 is inserted into the engaging hole 16 in order to secure the toothbrush section 6 on the holder.

Figure 3:
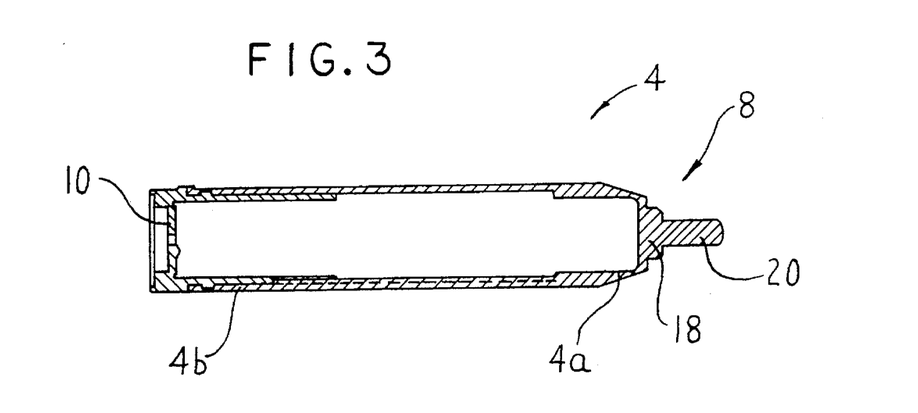
FIG. 3 is a center vertical section view of the holder section of the motor-driven toothbrush.
Figure 4:
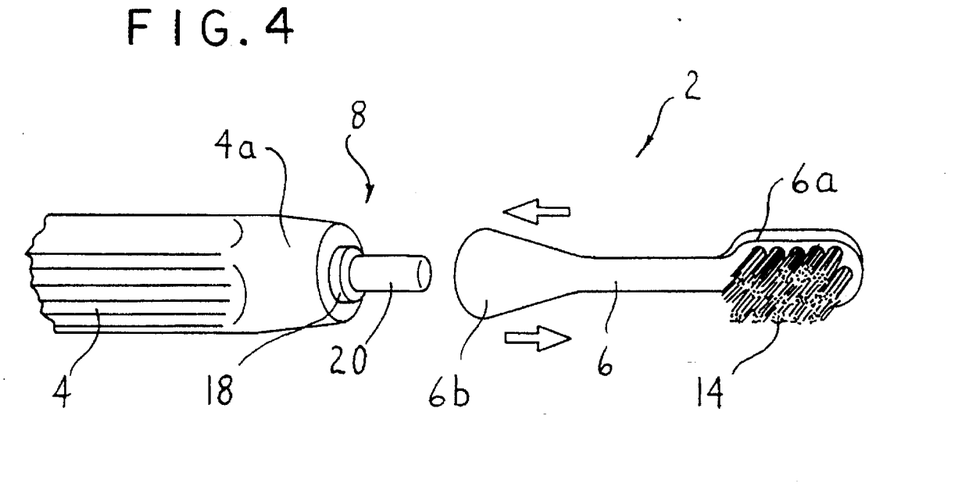
FIG. 4 is a general perspective view illustrating how the toothbrush section is inserted into the holder section of the motor-driven toothbrush.
Figure 5:
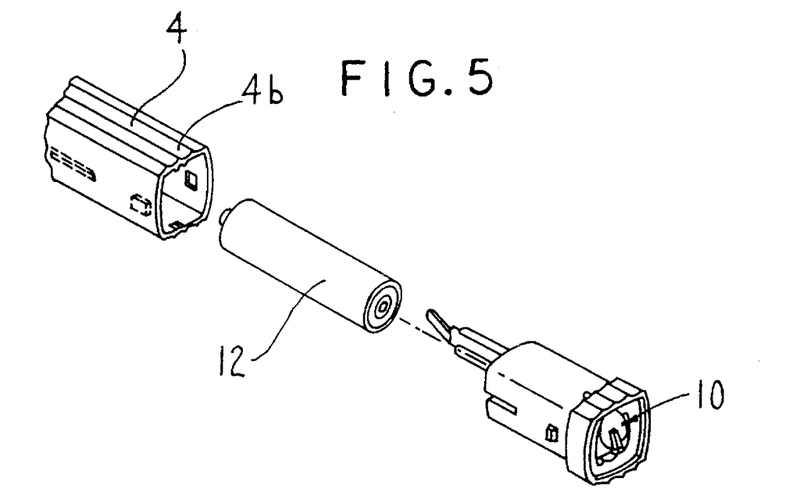
FIG. 5 is a general perspective view illustrating a state where a battery is incorporated in the holder section of the motor-driven toothbrush.
Figure 7:
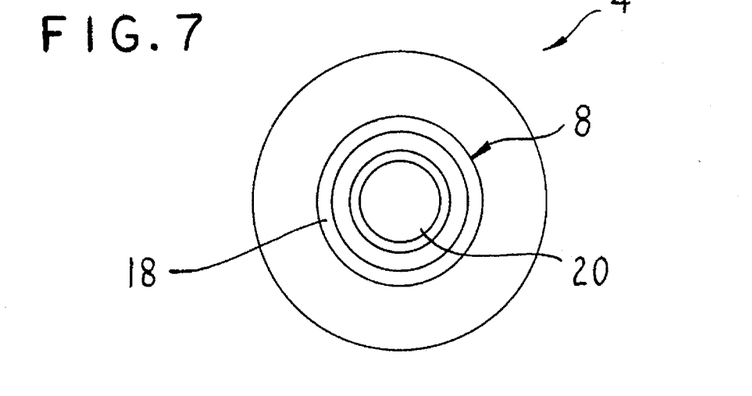
FIG. 7 is an enlarged view from a side of one end of the holder section of the motor-driven toothbrush.

To describe the invention in additional detail, the engaging projection section 8 is, as shown, in FIGS. 1, 3 and 7, formed with a large diameter stem section 18 and a tip projection 20 with a smaller diameter than that of the stem section 18. The large diameter stem section 18 and the tip projection 20 are made of plastic or like material and have a cylindrical shape. As used herein, D is the outer diameter of the tip projection 20.

Figure 8:
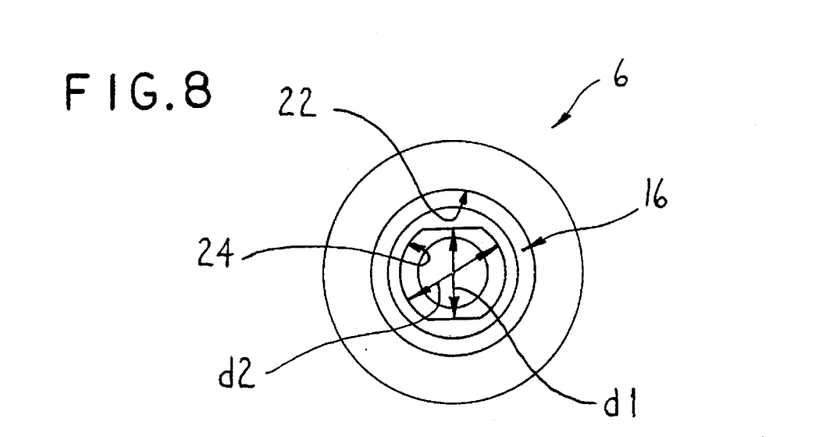
FIG. 8 is an enlarged view from a side of the other end of the toothbrush section of the motor-driven toothbrush.
Figure 9:
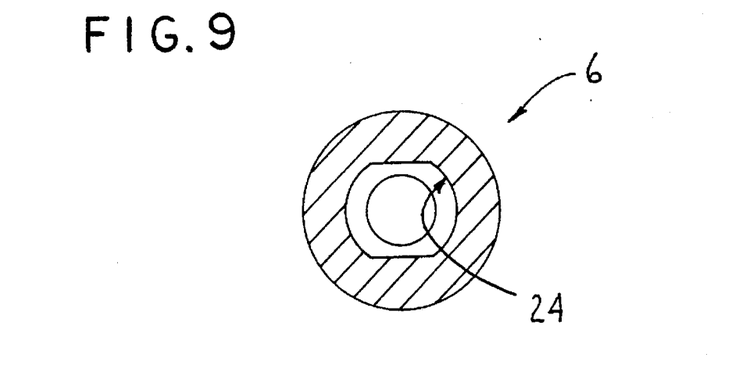
FIG. 9 is a cross-sectional view taken along the line between IX and IX in FIG. 1.

The engaging hole 16 of the toothbrush section 4 is, as shown in FIGS. 1, 8 and 9, defined by a large diameter section 22 in the entrance end thereof and a smaller diameter section 24 in the distal end thereof. The large diameter section 22 in the entrance end thereof and the smaller diameter section 24 in the distal side thereof are made of plastic material.

Furthermore, the smaller diameter section 24 in the bottom side has, as shown in FIG. 8, the top and the bottom surfaces each projecting like a flat plate, wherein d1 is a first inner diameter, namely a distance between the top side and the bottom side thereof and d2 is a second inner diameter, namely a distance between other surfaces thereof.

A relation between the outer diameter D of the point projection 20, the first inner diameter d1 and the second inner diameter d2 of the smaller diameter section 24 in the bottom side of the hole is set to satisfy the expression of $d1 < D \leq d2$.

When the engaging projection section 8 of the holder section 4 is inserted into the engaging hole 16 of the toothbrush section 6, the tip projection 20 is inserted thereinto while the smaller diameter section 24 in the distal end thereof is slightly expanded.

The toothbrush section 6 is thus firmly fixed on the holder section 4 to enable vibration, rolling movement or sliding movement of the toothbrush section by the drive unit.

With this feature, configuration of the engaging section between the holder section 4 and the toothbrush section 6 of the motor-driven toothbrush 2 is simplified. The manufacture, especially the molding of the engaging projection section 8 is relatively simple. This reduces the cost of providing the toothbrush of this invention.

Moreover, the design of the engaging section between the holder section 4 and the toothbrush section 6 of the toothbrush 2 offers an assembly that is both small in size and light in weight. These features make the toothbrush 2 more convenient to use.

Furthermore, when the tip projection 20 is inserted into the smaller diameter section 24 in the bottom side of the hole, the toothbrush section 6 is firmly fixed on the holder section 4 and there is little possibility that the toothbrush section 6 will disengage from the holder section 4.

Still furthermore, the engaging position between the holder section 4 and the toothbrush section 6 is not limited, so that a work for engaging the two components is quite easy, which is advantageous in actual use.

FIGS. 10 to 15 illustrate a second embodiment of the present invention. In this embodiment of the invention, the same reference numerals are assigned to the portions playing the same functions as those in the first embodiment.

The second embodiment is characterized in that the engaging projection section 8 in the engaging section of the holder section 4 is inserted into the engaging hole 16 to fix the toothbrush section 6.

The toothbrush section 6 is made of resilient material to define the engaging hole 16 with a round cross-sectional profile into which the engaging projection section 8 is inserted.

Also, the engaging hole 16 is provided for inserting the engaging projection section 8 in the engaging section of the holder section 4 thereinto and for fixing the toothbrush section 6 in the hole.

Figure 10:
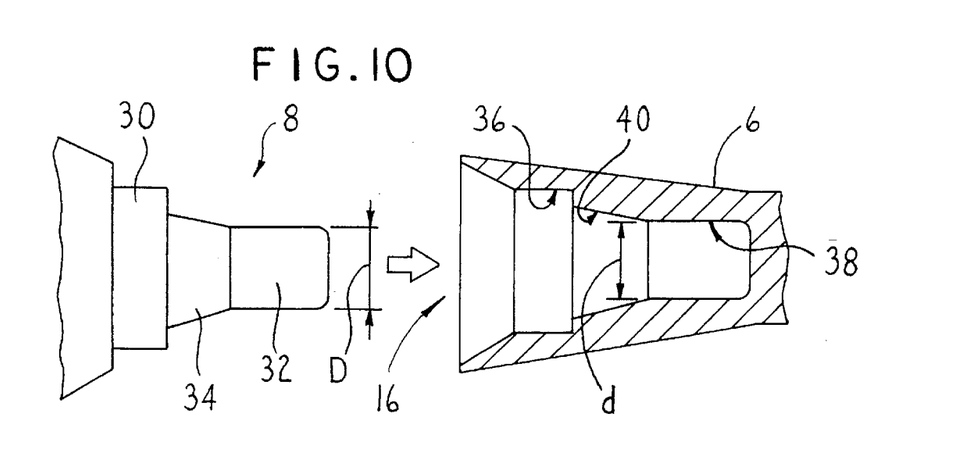
FIG. 10 is a general enlarged cross-sectional view illustrating a state where the toothbrush section has been inserted into the holder section of the motor-driven toothbrush according to the second embodiment of the present invention.
Figure 11:
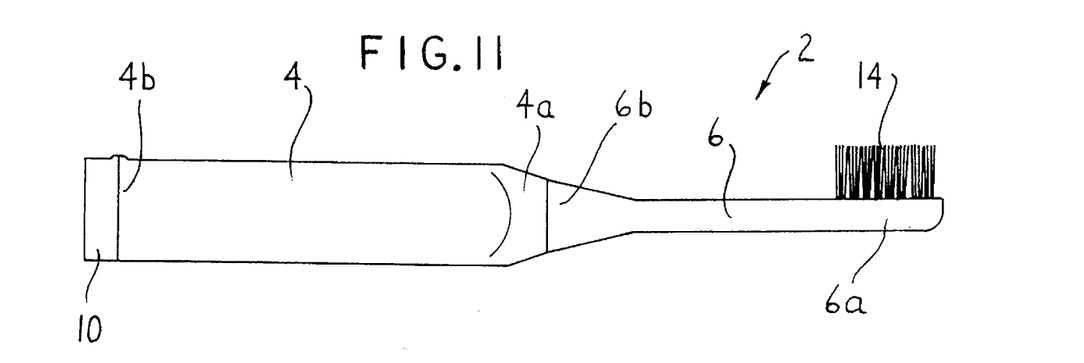
FIG. 11 is a front view of the motor-driven toothbrush.
Figure 12:
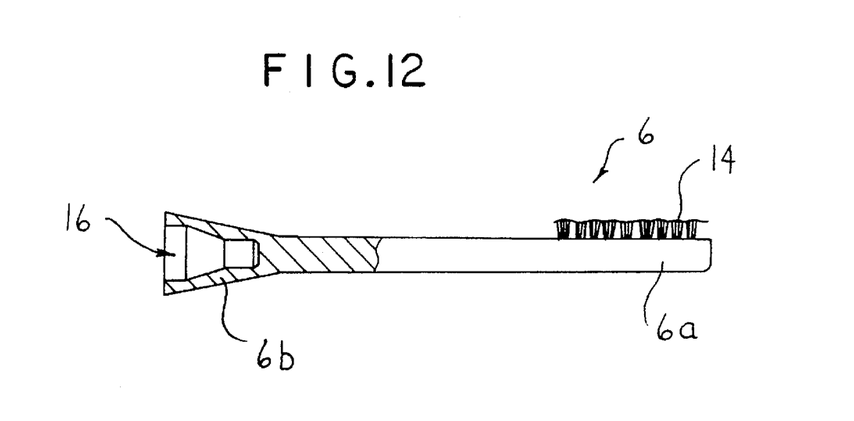
FIG. 12. is a portion cross-sectional and broken view of the toothbrush section of the motor-driven toothbrush.
Figure 13:
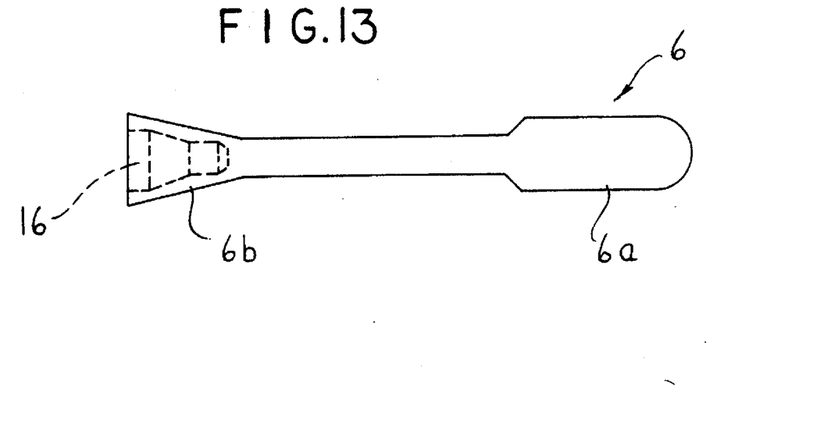
FIG. 13 is a rear view of the toothbrush section of the motor-driven toothbrush.
Figure 14:
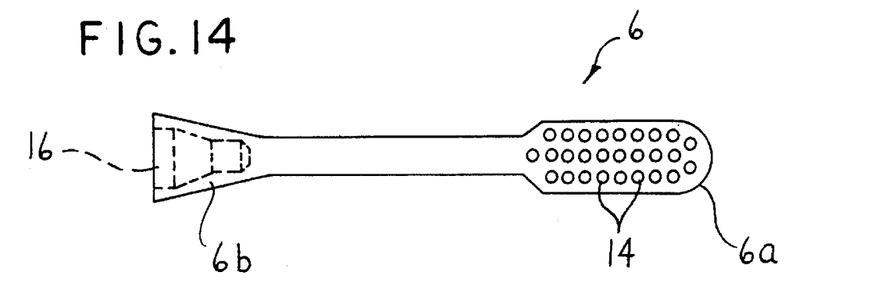
FIG. 14 is a front view of the toothbrush section of the motor-driven toothbrush.

The engaging projection section 8 of the second embodiment of this invention is formed, as shown in FIG. 10, with a large diameter stem section 30, a tip projection 32 with a smaller diameter than the large diameter stem section 30. A taper section 34 joins the large diameter stem section 30 and the tip projection 32. The large diameter stem section 30 and the tip projection 32 are formed with, for instance, plastic material into a cylindrical shape. Herein, D is the outer diameter of the tip projection 32.

The base of the toothbrush section 6 is made of, for instance, plastic material. The engaging hole section 16 is shaped to have a round cross-section comprising a large diameter section 36 in the entrance side of the hole, a small diameter section 38 in the bottom side thereof 38, and a tapered shape hole for jointing together the larger diameter section and the smaller diameter section, as shown in FIGS. 10 and 13 to 15.

Figure 15:
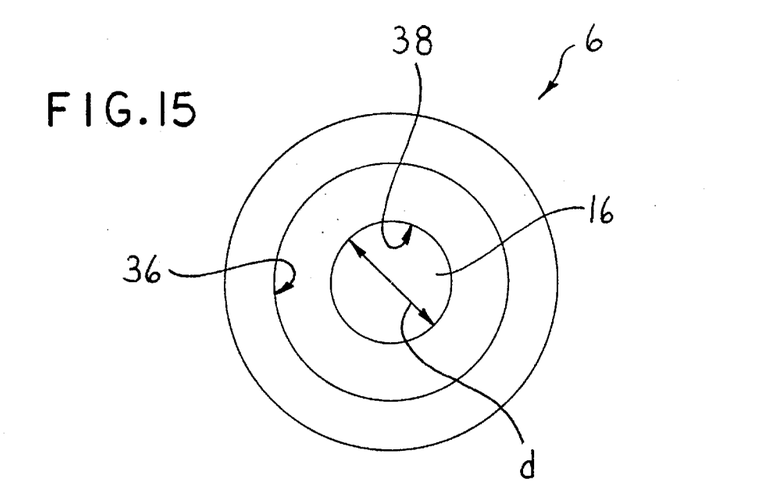
FIG. 15 is an enlarged view from a side of the other end of the toothbrush section of the motor-driven toothbrush.

Furthermore, the smaller diameter section in the distal end thereof 38 is, shown in FIG. 15, formed with a round cross-section, and a relation between the outer diameter D of the tip projection 32 and the inner diameter d of the smaller diameter section in the distal end 38 is formed to satisfy the expression of d<D.

When the engaging projection section 8 of the holder section 4 is inserted into the engaging hole 16 of the toothbrush section 6, the tip projection 32 is inserted thereinto while the smaller diameter section in the distal end of the hold 38 is slightly expanded.

The toothbrush section 6 is firmly fixed to the holder section 4, which enables vibration, rolling movement or sliding movement of the toothbrush section 6 by the drive unit.

Thus, the second embodiment of this invention offers cost advantages and ease of use advantages similar to those gained by the first embodiment of this invention.

Moreover, the tip projection 32 of the holder section 4 is inserted into the smaller diameter section in the bottom side of the hole 38 of the toothbrush section 6. Moreover, like with the first embodiment of the invention, the toothbrush section 6 of this embodiment is firmly fixed on the holder section 4, and there is little possibility that the toothbrush section 6 will disengage from the holder section 4 during use thereof.

Furthermore, the engaging position between the holder section 4 and the toothbrush section 6 is not limited to a specific position, and like in the first embodiment described above, a work for engaging the two components is quite easy, which is advantageous in an actual use.

Figure 16:
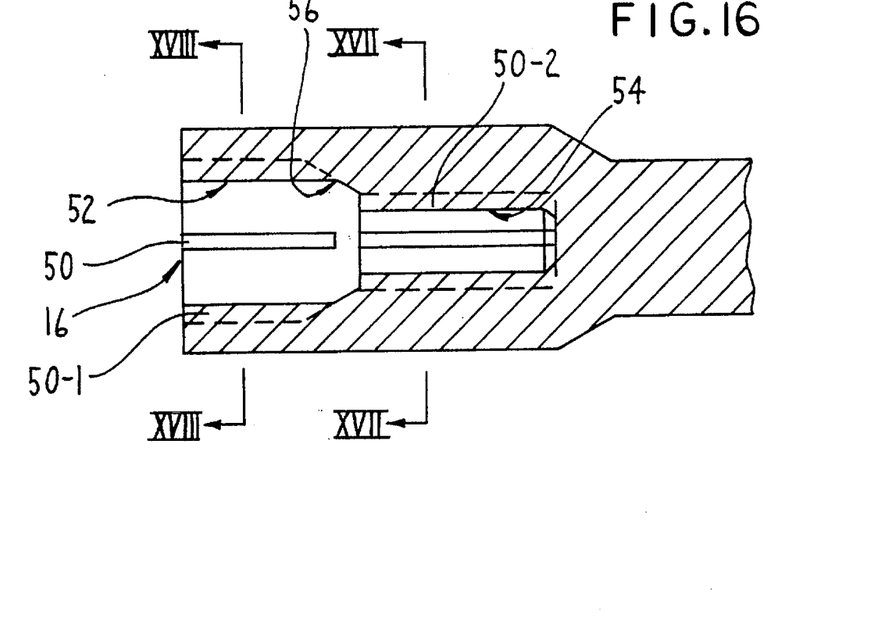
FIG. 16 is a general enlarged cross-sectional view of the toothbrush section illustrating the third embodiment according to the present invention.
Figure 17:
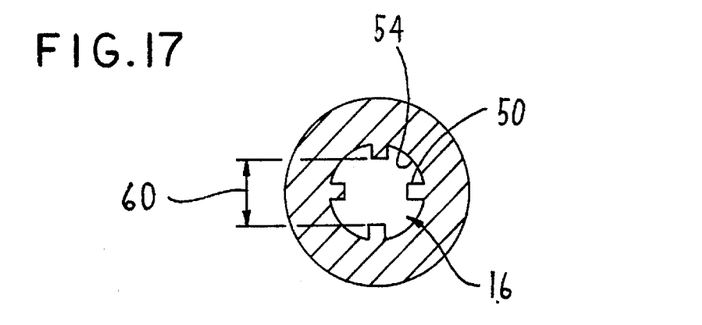
FIG. 17 is a cross-sectional view taken along the line between XVII and XVII in FIG. 16.
Figure 18:
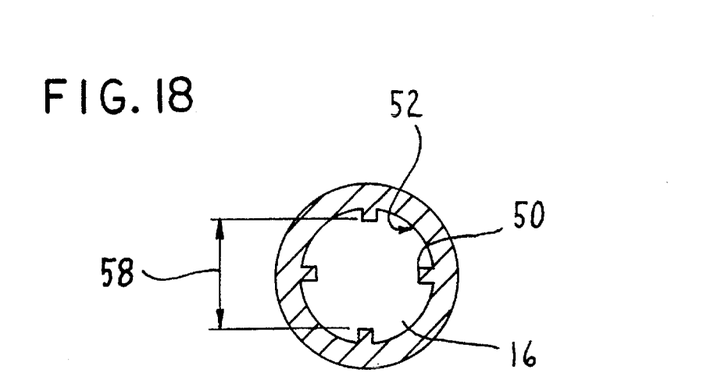
FIG. 18 is a cross-sectional view taken along the line between XVIII and XVIII in FIG. 16.

FIGS. 16 to 18 illustrate a third and preferred embodiment of the present invention. This embodiment of the invention is characterized in that, the toothbrush section 6 is shaped to have at least one engaging key 50 that projects into the center of the engaging hole 16.

The engaging hole 16 is formed with a larger diameter section 52 in the entrance end, a small diameter section 54 in the distal end thereof, and a tapered shaped hole section 56. At least one, and herein, four engaging keys 50 are provided that are equally spaced around the perimeter of the engaging hole 16.

Toothbrush section 6 is constructed so as to have a first set of elongate engaging keys 50-1 that project into the large diameter hole sections 52 and a second set of elongate engaging keys 50-2 that project into the smaller diameter hole section 54.

If the distance 58 between the two diametrically separated engaging sections of first keys 50-1 is less than the outer diameter of the larger diameter stem section 30 of projection section 8 and the distance 60 between the second keys 50-2 is less than the outer diameter of the tip projection 32, when an engaging projection section 8 of a holder section 6 (FIG. 10) is inserted into the engaging hole 16 of the toothbrush section, pressure engagement is realized by both first and second sets of keys 50-1 and 50-2, respectively.

If the distance between the two first keys 50-1 is less than the outer diameter of the stem section 30, and the distance between the second keys 50-2 is greater than the outer diameter of the tip projection 32, when the engaging projection section 8 of a holder section 4 is inserted into the engaging hole 16 of the toothbrush section, pressure engagement is realized by the first keys 50-1.

If the distance between the opposed first keys 50-1 is greater than the outer diameter of the larger diameter stem section 30 and the distance between the opposed tip engaging sections of the second keys 50-2 is less than the outer diameter of the tip projection 32, when an engaging projection section 8 of a holder section 4 is inserted into the engaging hole section 16 of the toothbrush section, pressure engagement is realized only by the second keys 50-2.

A number of the grooves (not shown) each suited for receiving the keys 50-1 and 50-2 are provided in the engaging projection section 8 which is an engaging section of a holder section 4 to be inserted into the engaging hole section 16.

Therefore, when inserting the engaging projection section of the holder section into the engaging hole of the toothbrush section to fix the toothbrush section on the holder section, the engaging projection section of the holder section can be held securely by the engaging section 50 including the first and second sets of projecting keys 50-1 and 50-2, respectively, and there is essentially no possibility that the toothbrush section 6 will disengage from the holder section during use thereof, and the reliability in insertion can be improved.

Also a position for engagement of the toothbrush section with the holder section is decided by a number of keys 50 so that a positional relation between the holder section and the toothbrush section is accurately defined, and the convenience in use thereof can be improved.

Furthermore, owing to the design of the engaging section between the holder section and the toothbrush section of the motor-driven toothbrush, the manufacture of this toothbrush becomes easier, enables cost reduction, and is economically advantageous.

This embodiment of the invention has similar desirable reduced size and weight characteristics as the other described embodiments of this invention.

It should be noted that the present invention is not limited to the disclosed embodiments and that other changes are possible.

For instance, although in the first described embodiment the cross-section of the smaller diameter hole section in the bottom side thereof which is an engaging hole in the toothbrush section of the motor-driven toothbrush is not round with the top and bottom surfaces thereof projecting like a flat shape respectively, other forms of a cross-sectional of the smaller diameter section in the bottom side are allowable provided that the cross-section includes at least in a portion thereof a portion having a smaller inner diameter section than an outer diameter of the tip projection of the holder section. For instance, a polygonal or star-shaped or other form of cross-section is allowable for the smaller diameter section in the bottom side.

Also with regard to the first embodiment of the present invention, the tip projection and the smaller diameter hole section in the distal end are engaged with each other. However, it is also possible for the larger diameter stem section provided in the holder section to engage the large diameter hole section in the entrance end provided in the toothbrush section 6.

The disclosed second embodiment of this invention is configured so that the tip projection 32 of the holder section 4 is inserted and engaged with the small diameter hole section 38 of the toothbrush section. However, the configuration is also allowable in which the large diameter stem section 30 is engaged with the large diameter hole section 36 in the entrance end of the toothbrush section 6. Also a configuration is allowable in which the tip projection 32 is engaged with the small diameter hole section 38 at the same time the large diameter stem section 30 is engaged with the large diameter hole section 36.

With regard to the third embodiment of this invention, four keys 50 are shown projecting into the engaging hole. It is possible to provide 1 to 3, or 5 or more keys. Also, while the illustrated keys 50 are directed toward the center of the engaging hole, in alternative embodiments of the invention the keys may have other shapes and orientations depending on the stress generated when the motor-driven toothbrush is used.

As described above, with the present invention, the engaging hole is formed in the engaging section of the toothbrush section of the motor-driven toothbrush, and the engaging projection section to be inserted into the engaging hole for fixing the toothbrush section on the holder section is provided in the engaging section of the holder section. This configuration of the engaging section between the holder section and the toothbrush section of the motor-driven toothbrush makes the manufacture of the toothbrush easier, so as to reduce its cost of manufacture. Also, the configuration of the engaging section between the holder section and the toothbrush section of the motor-driven toothbrush serves to reduce both the size and weight of the motor-driven toothbrush so as to enhance the convenience of its use. The same advantages are gained with the engaging projection 8 of the holder section. The engaging projection section is inserted into the engaging hole so that the toothbrush section is firmly fixed on the holder section, like a regular manual toothbrush. This makes it possible to avoid such disadvantages as that the toothbrush section is disengaged from the holder section during use thereof. The use of the key 50 to clamp the toothbrush section 6 over the holder section projection section 8 substantially eliminate the chance the toothbrush section will disengage from the holder section.

Although a particular preferred embodiments of the invention have been disclosed in detail for illustrative purposes, it will be recognized that variations or modifications of the disclosed apparatus, including the rearrangement of parts, tie within the scope of the present invention.

The embodiments of the invention in which an exclusive property or privilege is claimed are defined as follows:

1. A motorized toothbrush comprising:
    a holder section including an elongated body enclosing a drive unit and a projection attached to one end of said body, said drive unit connected to said projection for moving said projection in response to actuation of said drive unit, said projection having a stem with a predetermined first diameter, a tip with a predetermined second diameter, and a tapered part positioned between said stem and said tip, said first diameter being larger than said second diameter,
    a toothbrush section having opposed ends with a brush head positioned on one said end, and a receiving section integrally formed with the other said end, said receiving section being formed of flexible material and being shaped to define a sectioned bore therein, said sectioned bore having a first section with a predetermined third diameter positioned near said other end, a second section having a predetermined fourth diameter smaller than said third diameter, and a tapered third section positioned between said first and second sections, said first section receiving said stem therein, said second section receiving said tip therein, and said third section receiving said tapered part therein, and
    elongate key means fixedly secured to and extending lengthwise within one of said first and second sections and projecting radially inwardly from the respective predetermined diameter for compression securing of said projection in said receiving section.

2. The motorized toothbrush according to claim 1, further comprising a plurality of said key means circumferentially spaced from one another and extending lengthwise within said one section, said plurality of said key means causing compression securing of said projection in said receiving section.

3. The motorized toothbrush according to claim 1, further comprising said key means extending lengthwise within both of said first and second sections.

4. A motorized toothbrush comprising:
    a holder section including an elongated body enclosing a drive unit and a projection attached to one end of said body, said drive unit connected to said projection for moving said projection in response to actuation of said drive unit, said projection having a stem with a predetermined first diameter, a tip with a predetermined second diameter, and a tapered part positioned between said stem and said tip, said first diameter being larger than said second diameter,
    a toothbrush section having opposed ends with a brush head positioned on one said end, and a receiving section integrally formed with the other said end, said receiving section being formed of flexible material and being shaped to define a sectioned bore therein, said sectioned bore having a first section with a predetermined third diameter positioned near said other end, a second section having a predetermined fourth diameter smaller than said third diameter, and a tapered third section positioned between said first and second sections, said first section receiving said stem therein, said second section receiving said tip therein, and said third section receiving said tapered part therein, and
    a plurality of circumferentially spaced elongate key means fixedly secured to and extending lengthwise along said first section and projecting radially inwardly of said third diameter for compression securing of said projection in said receiving section, said plurality of key means defining therein a clearance diameter in said first section measured between radial inner edges of said key means, said clearance diameter being larger than said fourth diameter.

5. The motorized toothbrush according to claim 4, wherein said plurality of circumferentially spaced elongate key means are fixedly secured to and extend lengthwise along said second section and project radially inwardly of said fourth diameter.

* * * * *